United States Patent
Contolini et al.

(10) Patent No.: US 9,293,141 B2
(45) Date of Patent: Mar. 22, 2016

(54) MULTI-USER VOICE CONTROL SYSTEM FOR MEDICAL DEVICES

(71) Applicant: Storz Endoskop Produktions GmbH, Tuttlingen (DE)

(72) Inventors: Matteo Contolini, Santa Barbara, CA (US); Ted Applebaum, Santa Barbara, CA (US)

(73) Assignee: Storz Endoskop Produktions GmbH, Tuttlingen (DE)

( * ) Notice: Subject to any disclaimer, the term of this patent is extended or adjusted under 35 U.S.C. 154(b) by 41 days.

(21) Appl. No.: 14/227,661

(22) Filed: Mar. 27, 2014

(65) Prior Publication Data

US 2015/0279368 A1 Oct. 1, 2015

(51) Int. Cl.

| | |
|---|---|
| *G10L 15/32* | (2013.01) |
| *G10L 15/22* | (2006.01) |
| *G10L 17/22* | (2013.01) |
| *G10L 15/14* | (2006.01) |
| *G10L 15/00* | (2013.01) |
| *G10L 17/00* | (2013.01) |
| *G10L 15/08* | (2006.01) |
| *A61B 1/00* | (2006.01) |
| *A61B 5/00* | (2006.01) |

(52) U.S. Cl.
CPC ............ *G10L 17/22* (2013.01); *A61B 1/00041* (2013.01); *A61B 5/00* (2013.01); *G10L 15/00* (2013.01); *G10L 15/08* (2013.01); *G10L 15/142* (2013.01); *G10L 15/32* (2013.01); *G10L 17/00* (2013.01)

(58) Field of Classification Search
USPC ........................................................ 704/275
See application file for complete search history.

(56) References Cited

U.S. PATENT DOCUMENTS

| | | | |
|---|---|---|---|
| 4,922,538 A | 5/1990 | Tchorzewski | |
| 6,308,158 B1 | 10/2001 | Kuhnen et al. | |
| 6,463,361 B1 * | 10/2002 | Wang et al. | 700/258 |
| 6,842,510 B2 * | 1/2005 | Sakamoto | 379/102.01 |
| 7,752,050 B1 * | 7/2010 | Hameed et al. | 704/275 |
| 7,899,669 B2 | 3/2011 | Gadbois | |
| 8,688,459 B2 * | 4/2014 | Nenov et al. | 704/275 |
| 8,709,009 B2 * | 4/2014 | Hamel | 606/41 |
| 2006/0136220 A1 | 6/2006 | Gurram et al. | |
| 2011/0161077 A1 | 6/2011 | Bielby | |
| 2011/0301952 A1 | 12/2011 | Koshinaka et al. | |
| 2015/0106085 A1 * | 4/2015 | Lindahl | 704/231 |

\* cited by examiner

*Primary Examiner* — Abul Azad
(74) *Attorney, Agent, or Firm* — Whitmyer IP Group LLC (57) ABSTRACT

The system includes a controller having first and second speech recognition modules and a decision module. The system includes at least one medical device operable by the controller. The system includes a first microphone in communication with the first speech recognition module, and a second microphone in communication with the second speech recognition module. The first speech recognition module generates a first set of commands from voice signals it receives from the first microphone. The second speech recognition module generates a second set of commands from voice signals it receives from the second microphone. The decision module receives the first and second sets of commands, accepts a subset of the commands in the first and second sets, rejects the remainder of the commands, and assembles a third set of commands comprising the accepted commands. The controller executes the third set of commands to operate the at least one medical device.

29 Claims, 5 Drawing Sheets

MULTI-USER VOICE CONTROL SYSTEM FOR MEDICAL DEVICES

FIELD OF THE INVENTION

The apparatuses and methods described herein generally relate to the field of voice controlled medical systems; and, more directly, to the field of such medical systems operable by multiple users.

BACKGROUND OF THE INVENTION

Modern operating rooms for performing surgery have seen several advancements over the past two decades. In the late $20^{th}$ century, state-of-the-art operating rooms included several electronic surgical instruments (i.e. electrosurgical units, insufflators, endoscopes, etc.). These instruments were separately operated by the surgeon and members of the surgical team. The industry improved upon this type of operating room by integrating the various instruments into a unified system. With this configuration, the surgeon and/or members of the team use a central controller (or surgical control unit) to control all of the instruments through a single interface (often a graphical-user interface). Generally speaking, these central control units were built using modified personal computers and the operating rooms using them are commonly referred to as "digital operating rooms".

The establishment of the digital operating room paved the way for the voice controlled operating room. With this system, a member of the surgical team (usually the surgeon) wears a headset with a microphone. The surgeon issues spoken commands into the headset, these commands are sent to the central controller that controls the various instruments to perform desired tasks or make on-the-fly adjustments to operating parameters. The central controller operates software including a speech-to-text converter (i.e. speech recognition software) to interpret and execute the voice commands. Since computers often have difficulty understanding spoken language, typical systems include audible confirmation feedback to the surgical team, notifying them that a command has been understood and executed by the controller. Since sterility is critically important in all surgical procedures, this touch-free control system represented a significant advancement.

The voice-controlled digital operating room was further improved by the introduction of the wireless voice-control headset. This gave the surgeon greater mobility and eliminated the microphone cable as a possible source of contamination or nuisance for the surgeon. Voice controlled digital operating rooms with wireless headsets represent the modern state-of-the-art in the field. Although this type of system has worked well for the convenience and efficacy of the surgical team and the maintenance of sterility, it has a few drawbacks.

By using ambient microphones, the wireless headset is eliminated as a potential source of contamination. However, the use of ambient microphones introduces new problems. Ambient microphone voice control systems use similar speech recognition software as headset voice control systems. It would be further advantageous for a voice controlled medical system to be able to receive simultaneous commands from multiple users, because multiple members of a medical team could efficiently take multiple actions simultaneously during an operation. For example, it would be advantageous for a nurse or surgeon's assistant to be able to control peripheral device functions while a surgeon simultaneously conducts an operation using only devices centrally important to the task at hand. This would reduce the workload of the surgeon and would allow the surgeon to dedicate all efforts to critically important tasks. As a result, total operation time and the frequency of surgical errors could be reduced.

However, state-of-the-art voice control systems are not capable of receiving and executing simultaneous commands from multiple users. Typically, only a single wireless headset is paired to each system and the wireless headsets do not pick up significant audio from distant sources. Thus, wireless headset systems can only receive commands from one user at a time. Ambient microphone systems can receive commands from multiple users in an environment. However, they usually exhibit poorer signal quality and voice recognition and cannot distinguish between multiple sources of commands. As a result, they are usually programmed to reject multiple simultaneous commands as a safety feature. If the system fails to reject commands from multiple users, it puts the patient at risk of suffering injury due the medical system taking undesired actions.

U.S. Pat. No. 7,752,050 to Hameed et al. describes a system capable of executing commands from multiple users. However, this system uses a simple switching mechanism to alternate between the audio channels of the two users. Although this system can preferentially execute commands from one of the users (i.e. by locking out the other channel when simultaneous commands are received), it cannot intelligently parse and execute simultaneous commands. Therefore, true simultaneous multi-user instrument control is not achieved.

There remains a need in the art for a voice controlled surgical system that can safely execute simultaneous commands from multiple users.

SUMMARY OF THE INVENTION

A multi-user voice controlled medical system includes a controller having a first speech recognition module, a second speech recognition module, and a decision module. The system further includes at least one medical device operable by the controller. The system further includes a first microphone in communication with the first speech recognition module. The system further includes a second microphone in communication with the second speech recognition module. The first speech recognition module generates a first set of commands from voice signals it receives from the first microphone. The second speech recognition module generates a second set of commands from voice signals it receives from the second microphone. The decision module receives the first and second sets of commands, accepts a subset of the commands in the first and second sets, rejects the remainder of the commands, and assembles a third set of commands comprising the accepted commands. The controller executes the third set of commands to operate the at least one medical device.

In some embodiments, the first speech recognition module adds commands to the first set of commands only if the voice signals it receives from said first microphone match a pre-approved user's voice. In some embodiments, the decision module accepts or rejects at least one command based on which of the first and second sets of commands it is in. In some embodiments, the decision module accepts or rejects at least one command based on whether the command conflicts with a command in a different set of commands. In some embodiments, a display module generates a visible alert when the decision module determines that a command conflicts with a command in a different set. In some embodiments, a sound generating module generates an audible alert when the decision module determines that a command conflicts with a command in a different set. In some embodiments, the decision module accepts or rejects at least one command based on instructions from a user. In some embodiments, the decision module accepts or rejects at least one command based on a risk of an unsafe condition resulting from that command being executed in combination with a command in a different set. In some embodiments, a display module generates a visible alert when the decision module determines that a risk of an unsafe condition would result from a command being executed in combination with a command in a different set. In some embodiments, a sound generating module generates an audible alert when the decision module determines that a risk of an unsafe condition would result from a command being executed in combination with a command in a different set. In some embodiments, the first and second microphones are components of wireless voice control headsets. In some embodiments, the first and second microphones are environment microphones. In some embodiments, the at least one medical device is an insufflator, a suction device, a light source, a video camera, a video control unit, a pressure gauge, a pump, an electrosurgical unit, a surgical table, a telephone, room lights, a personal digital assistant, a room camera, or an endoscope.

A method of operating at least one medical device using voice commands from multiple users includes receiving a plurality of first voice signals from a first microphone. The method further includes recognizing a first set of commands from the first voice signals using a first speech recognition module. The method further includes receiving a plurality of second voice signals from a second microphone. The method further includes recognizing a second set of commands from the second voice signals using a second speech recognition module. The method further includes accepting a subset of commands from the first and second sets of commands and rejecting the remainder of the commands from the first set and second sets of commands. The method further includes assembling a third set of commands using the commands accepted. The method further includes executing the third set of commands to operate at least one medical device.

In some embodiments, the method further comprises comparing the first voice signals to a pre-approved user's voice. In some embodiments, the second step is only performed if the first voice signals match a pre-approved user's voice. In some embodiments, a command is accepted or rejected based on which of the first and second sets of commands it is in. In some embodiments, a command is accepted or rejected based on whether the command conflicts with a command in a different set of commands. In some embodiments, the method further includes determining if a command in one set of commands conflicts with a command in a different set of commands and issuing an alert if a conflict is found. In some embodiments, the method further includes rejecting one of the conflicting commands upon being commanded to do so by a user. In some embodiments, the alert is a visible alert. In some embodiments, the alert is an audible alert. In some embodiments, a command is accepted or rejected based on a risk of an unsafe condition resulting from that command being executed in combination with a command in a different set. In some embodiments, the method further includes determining if there is a risk of an unsafe condition resulting from a command being executed in combination with a command in a different set a command and issuing an alert if a risk is found. In some embodiments, the method further includes rejecting at least one of the commands upon being commanded to do so by a user. In some embodiments, the first and second microphones are components of wireless voice control headsets. In some embodiments, the first and second microphones are environment microphones. In some embodiments, the at least one medical device is an insufflator, a suction device, a light source, a video camera, a video control unit, a pressure gauge, a pump, an electrosurgical unit, a surgical table, a telephone, room lights, a personal digital assistant, a room camera, or an endoscope.

DETAILED DESCRIPTION OF THE INVENTION

Figure 1:
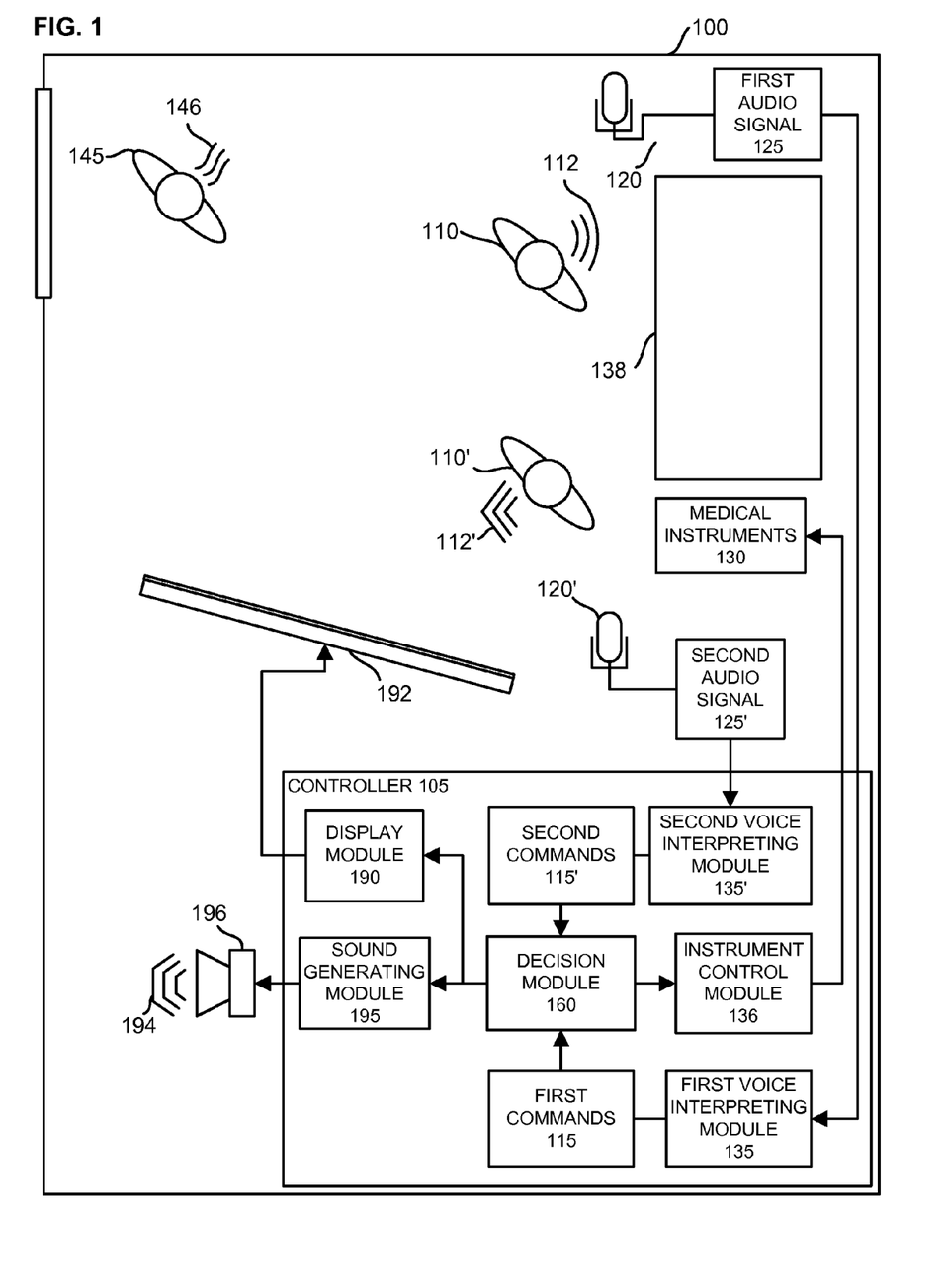
FIG. 1 is a block diagram of one embodiment of the multi-user voice controlled medical system in an operating environment using ambient microphones.

FIG. 1 shows an operating environment 100 with a multi-user voice controlled medical system located therein. During a medical procedure, operators 110, 110' issue operator speech 112, 112' that is received by ambient microphones 120, 120'. First voice interpreting module 135 in controller 105 interprets first operator speech 112 from first audio signal 125 to identify first commands 115. Second voice interpreting module 135' in controller 105 interprets second operator speech 112' from second audio signal 125' to identify second commands 115'.

Decision module 160 analyzes first commands 115 and second commands 115'. Based on the content of commands 115, 115' and the operator 110, 110' issuing commands 115, 115', decision module 160 rejects some of commands 115, 115' and accepts other commands 115, 115'. Furthermore, decision module 160 determines the order and timing with which accepted commands 115, 115' will be executed. Decision module 160 forwards the sequence of commands 115, 115' to instrument control module 136.

Controller 105 uses instrument control module 136 to send instructions to medical instruments 130 based on the sequence of commands 115, 115' from decision module 160. Medical instruments 130 are typically connected to a patient on surgical table 138. Medical instruments 130 may include, for example, an insufflator, a suction device, a light source, a video camera, a video control unit, a pressure gauge, a pump, an electrosurgical unit, a surgical table, a telephone, room lights, a personal digital assistant, a room camera, or an endoscope. In this way, operators 110, 110' (who may be, for example, a surgeon and nurse) can perform an operation on a patient on surgical table 138 while controlling medical instruments 130 using voice commands 115, 115'.

In some embodiments, display 192 in operating environment 100 displays which commands 115, 115' were executed from each operator 110, 110'. Display 192 is driven by display module 190 that receives information about which commands 115, 115' were executed from decision module 160. Operators 110, 110' can determine which of their commands 115, 115' were executed to control medical instruments 130 by viewing display 192. Operators 110, 110' can also determine which commands 115, 115' were executed by listening for verification sound 194. Verification sound 194 is generated by speaker 196 in operating environment 100. Sound generating module 195 operates speaker 196 to issue verification sound 194 based on information it receives from decision module 160. For example, sound generating module 195 may emit one sound 194 every time a command 115 from first operator 110 is executed and a different sound 194 ever time a command 115' from second operator 110' is executed. This way operators 110, 110' can keep track of which commands 115, 115' have been executed, even though controller 105 is executing a combination of their commands 115, 115' and rejecting some of those commands 115, 115'.

Voice interpreting modules 135, 135' use speech recognition algorithms, such as hidden Markov model (HMM) analysis, to interpret operator speech 112. Operator speech 112, 112' (within audio signals 125, 125') comprise sequences of sounds—voice interpreting modules 135, 135' determine the order of the sequences to determine the words contained in operator speech 112, 112'. In embodiments that perform HMM analysis, voice interpreting modules 135, 135' interpret speech 112, 112' using voice interpreting data and look-up tables of sound patterns and corresponding words. In some embodiments, voice interpreting data are developed prior to installation in operating environment 100 using clean speech samples.

Noise can be generated by medical instruments 130 or other devices; persons 145 may also produce third-party speech 146 or other noise in operating environment 100. Controller 105 may use the stereo input from array signals 125, 125' to perform noise reduction or cancellation. A lower or higher correlation threshold can be applied in certain domains if it improves performance, such as the signal, spectrum, log-Mel-spectrum, or Mel-frequency cepstrum domain. In some embodiments, voice interpreting modules 135, 135' and/or decision module 160 use recognizer output voting error reduction (ROVER) using both array signals 125, 125' to improve voice recognition performance.

In order to dedicate each voice interpreting module 135, 135' to each user 110, 110', each voice interpreting module 135, 135' can identify each user 110, 110' by their voice. Once such identification has taken place, each voice interpreting module 135, 135' can ignore speech 112, 112', 146 from all but a single individual 110, 110', 146. This will improve performance by ensuring that each channel or voice interpreting module 135, 135' is dedicated to a single user 110, 110'. For example, in FIGS. 1 and 2, first voice interpreting module 135 would substantially only interpret speech commands 112 from first user 110, and second voice interpreting module 135' would substantially only interpret speech commands 112' from second user 110'. In some embodiments, decision module 160 can reject commands 115, 115' if the identity of the person 110, 110', 145 who produced the speech 112, 112', 146 does not match the voice interpreting module 135, 135' that the command 115, 115' is sent from.

Figure 2:
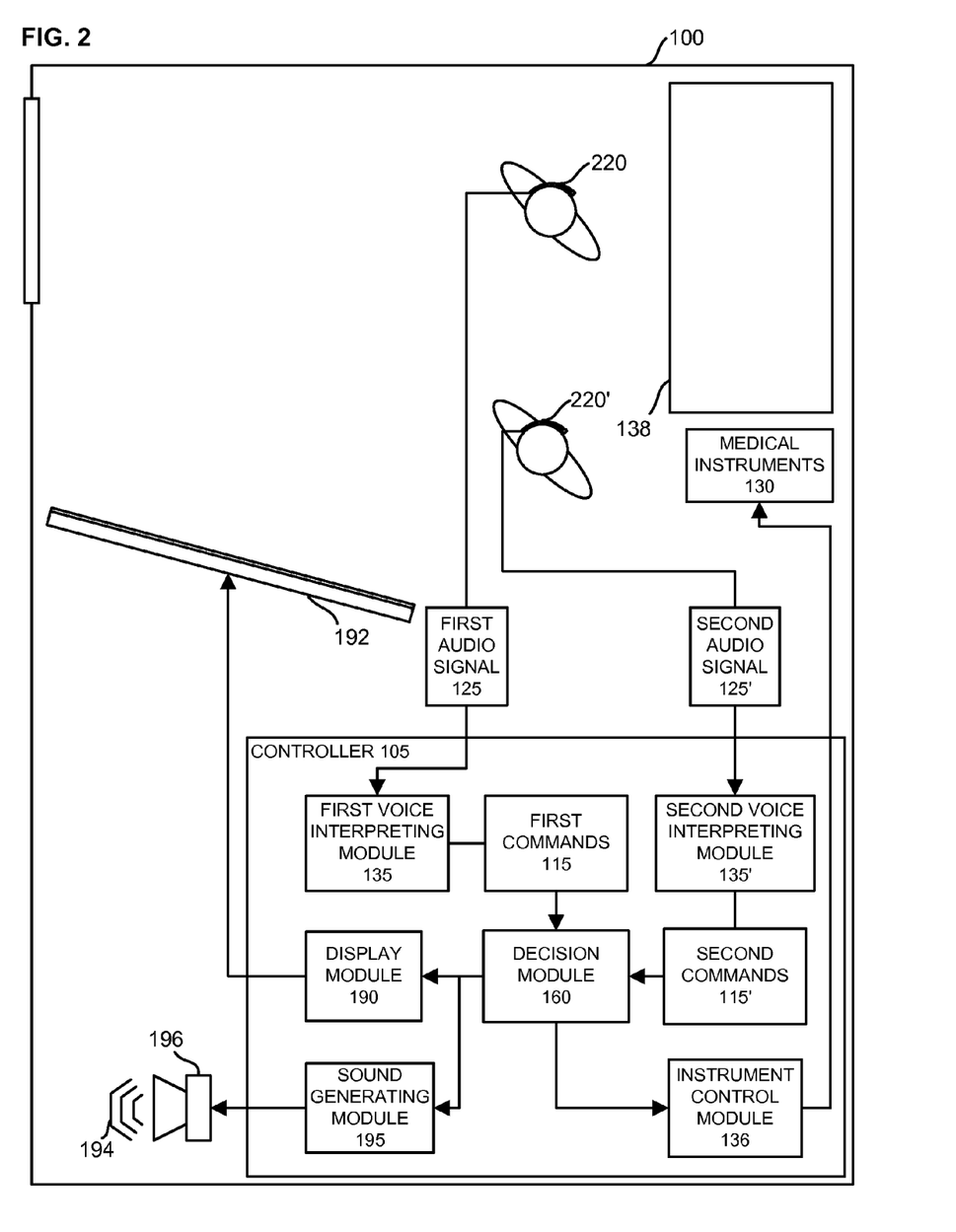
FIG. 2 is a block diagram of the embodiment of the multi-user voice controlled medical system of FIG. 1 in an operating environment using close-talking microphones.

Accepting or rejecting speech 112, 112', 146 or commands 115, 115' based on the issuer identity improves both performance and security. Firstly the noise rejecting capability of the system is improved because unwanted speech 146 and noise is ignored. Secondly, performance is improved because voice interpreting modules 135, 135' only interpret speech 112, 112' from desired users (thus preventing computing resources being wasted interpreting unwanted speech). Thirdly, security is improved because unauthorized personnel 145 are prevented from controlling the system.

FIG. 2 is a block diagram of the embodiment of the multi-user voice controlled medical system of FIG. 1 in an operating environment 100 using close-talking microphones 220, 220'. During a medical procedure, operators 110, 110' issue operator speech 112, 112' that is received by close-talking microphones 220, 220'. In some embodiments, close-talking microphones 220, 220' are components of wireless voice control headsets. In this embodiment, noise is further reduced because of the high signal-to-noise ratio of close-talking microphones 220, 220'. Furthermore, it is easier to isolate the speech recognition functions of voice interpreting modules 135, 135' such that each module 135, 135' or channel is fully dedicated to each user 110, 110'.

Figure 3:
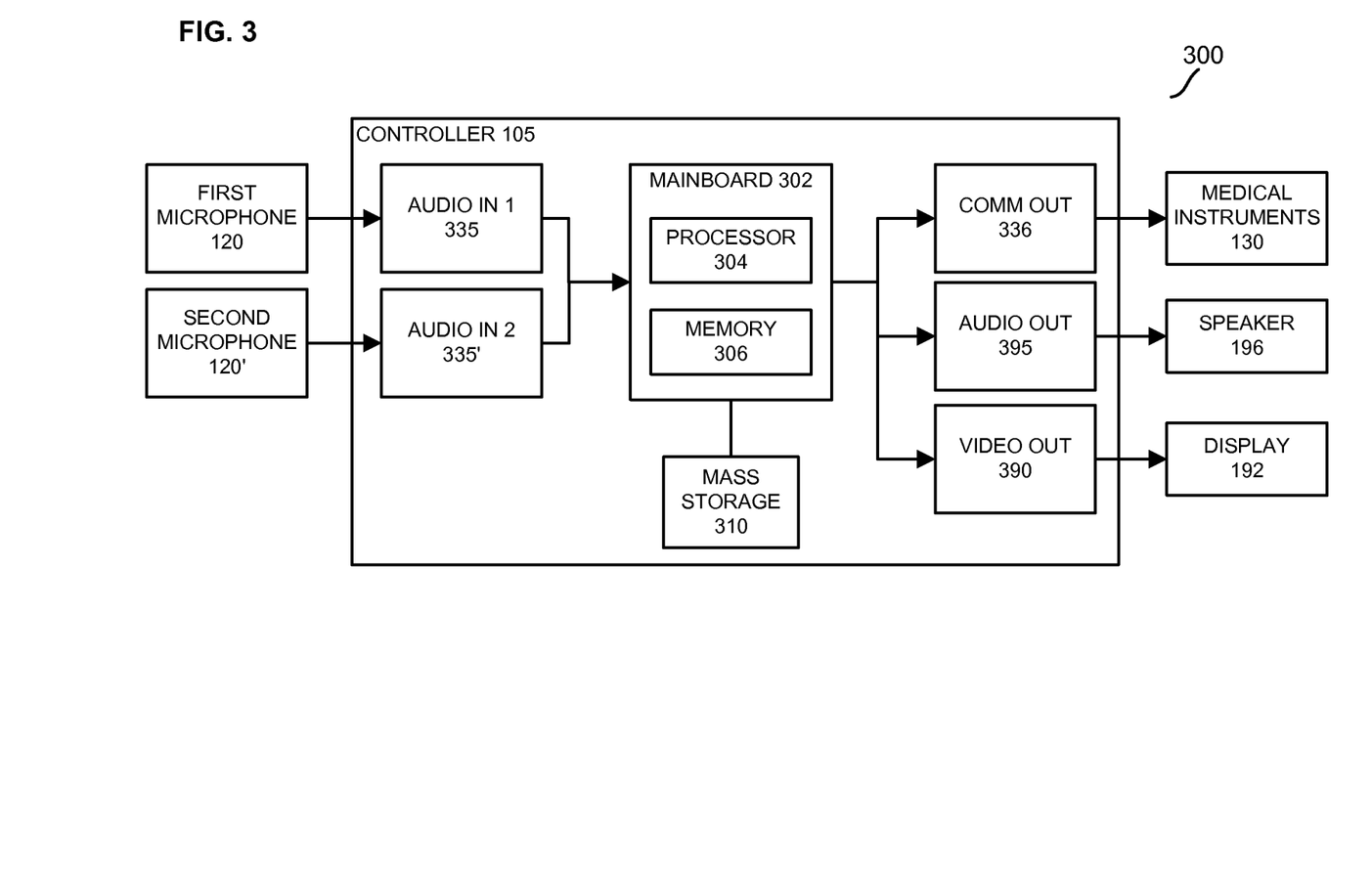
FIG. 3 is a block diagram of the hardware of one embodiment of the multi-user voice controlled medical system of FIG. 1.

FIG. 3 is a block diagram of the hardware of one embodiment of the multi-user voice controlled medical system 300 of FIG. 1. Controller 105 comprises two audio inputs—Audio In 1 335 and Audio In 2 335'. The two audio inputs 335, 335' are connected to first microphone 120 and second microphone 120', respectively. In some embodiments, audio inputs 335, 335' convert audio data from microphones 120, 120' from an analog to a digital format. In some embodiments, audio inputs 335, 335' comprise processors and memory executing software that interprets voice commands 115, 115' in the audio data from microphones 120, 120'.

Controller 105 comprises a mainboard 302 having a processor 304 and memory 306. Processor 304 may comprise one or more microprocessors, microcontrollers, application specific integrated circuits, programmable logic devices, programmable gate arrays, etc . . . Memory 306 may include any combination of one or more random access memories, read only memories (which may be programmable), flash memory, and/or similar storage devices. Controller 105 also comprises mass storage 310 that stores data and software that may not be currently in use. Mass storage 310 may comprise a hard disk drive, solid state drive, flash memory, optical storage media, and/or similar storage devices. System 300 is capable of buffering commands 115, 115' on memory 306, mass storage 310, or elsewhere. This buffering capability allows decision module 160 to analyze a list of commands 115, 115' simultaneously.

Software on memory 306 is executed by processor 304. In some embodiments, processor 304 and memory 306 on mainboard 302 interpret voice commands 115, 115' in the audio data from audio inputs 335, 335'. In some embodiments, processor 304 and memory 306 execute software that decides which commands 115, 115' in audio data from audio inputs 335, 335' to execute, the execution order of selected commands 115, 115', and when to execute selected commands 115, 115'.

In some embodiments, processor 304 and memory 306 also execute software that executes commands 115, 115'. Controller 105 uses comm out 336 to send instructions to medical instruments 130 based on commands 115, 115' that have been selected for execution. Comm out 336 may comprise a digital to analog converter that converts digital instructions from processor 304 and mainboard 302 into analog signals that convey instructions to medical instruments 130. In some embodiments, comm out 336 converts digital signals from processor 304 and mainboard 302 into digital signals of a different format. In some embodiments, comm out 336 sends signals to medical instruments 130 using a communication standard such as RS-232, USB, Bluetooth, 802.11, Infrared, Ethernet, FireWire, Thunderbolt, Storz Communication Bus (SCB), or other protocol.

Audio out 395 sends audio signals to speaker 196 to communicate audio information to operators 110, 110'. In some embodiments, audio out 395 sends an analog audio signal to speaker 196, and speaker 196 converts the audio signal into audible sounds. In some embodiments, audio out 395 and speaker 196 produce verification sound 194 to alert operators 110, 110' that a command 115, 115' has been accepted and/or executed, and from whom the command 115, 115' was issued. In some embodiments, audio out 395 and speaker 196 produce an audible alert to alert operators 110, 110' that a command 115, 115' has been rejected, or a combination of commands 115, 115' is contradictory, duplicative, or would result in an unsafe condition.

Video out 390 sends video signals to display 192 to communicate video information to operators 110, 110'. In some embodiments, video out 390 sends an analog video signal (over an analog interface such as VGA, DVI-A, Composite, Component, S-Video, SCART, etc . . . ) to display 192, and display 192 converts the video signal into images. In some embodiments, video out 390 sends a digital video signal (over a digital interface such as SDI, DVI-D, HDMI, DisplayPort, FPD-Link, Thunderbolt, FireWire, etc . . . ) to display 192. In some embodiments, video out 390 and display 192 alert operators 110, 110' that a command 115, 115' has been accepted and/or executed, and from whom the command 115, 115' was issued. In some embodiments, video out 390 and display 192 produces a visible alert to alert operators 110, 110' that a command 115, 115' has been rejected, or a combination of commands 115, 115' is contradictory, duplicative, or would result in an unsafe condition.

It should be understood that voice interpreting modules 135, 135', sound generating module 195, decision module 160, instrument control module 136, and display module 190 may be discrete hardware components (i.e. microprocessors, microcontrollers, application specific integrated circuits, programmable logic devices, programmable gate arrays, PCI, PCIe, or AGP boards, etc . . . ), or they may be software executing on a computer (i.e. software on memory 306 being executed by processor 304).

Figure 4:
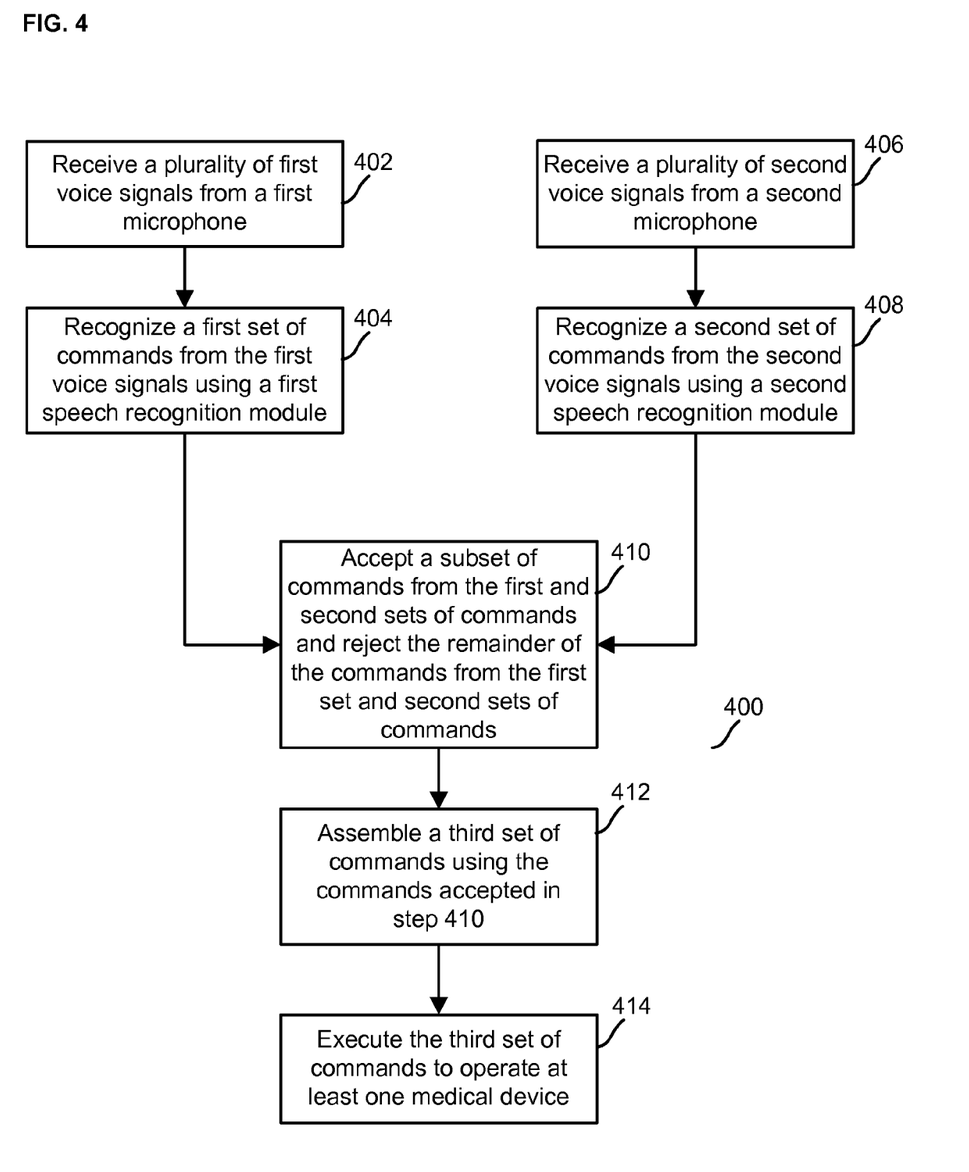
FIG. 4 is a method of operating at least one medical device using voice commands from multiple users according to one embodiment.

FIG. 4 shows a method operating at least one medical device using voice commands from multiple users according to one embodiment (400). The method 400 includes receiving a plurality of first voice signals from a first microphone (402). The method 400 further includes recognizing a first set of commands from the first voice signals using a first speech recognition module (404). The method 400 further includes receiving a plurality of second voice signals from a second microphone (406). The method 400 further includes recognizing a second set of commands from the second voice signals using a second speech recognition module (408). The method 400 further includes accepting a subset of commands from the first and second sets of commands and rejecting the remainder of the commands from the first set and second sets of commands (410). The method 400 further includes assembling a third set of commands using the commands accepted in step 410 (412). The method 400 further includes executing the third set of commands to operate at least one medical device (414).

Figure 5:
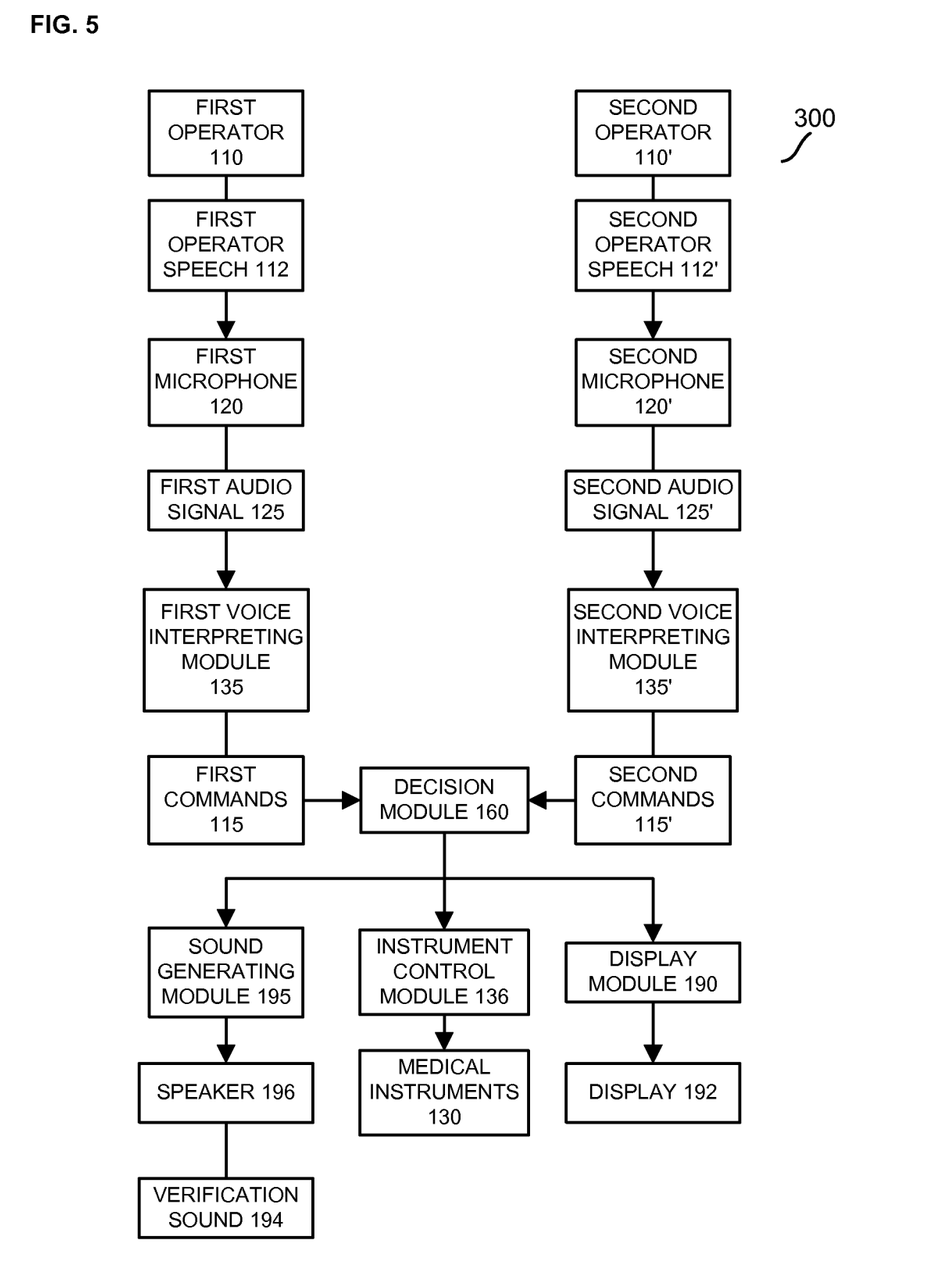
FIG. 5 is a block diagram of the embodiment of the multi-user voice controlled medical system of FIG. 1 in operation.

FIG. 5 is a block diagram of the embodiment of the multi-user voice controlled medical system 300 of FIG. 1 in operation. During a medical procedure, operators 110, 110' issue operator speech 112, 112' that is received by microphones 120, 120'. First voice interpreting module 135 interprets first operator speech 112 from first audio signal 125 to identify first commands 115. Second voice interpreting module 135' interprets second operator speech 112' from second audio signal 125' to identify second commands 115'.

Decision module 160 analyzes first commands 115 and second commands 115'. Based on the content of commands 115, 115' and the operator 110, 110' issuing commands 115, 115', decision module 160 rejects some of commands 115, 115' and accepts other commands 115, 115'. Furthermore, decision module 160 determines the order that accepted commands 115, 115' should be executed. Decision module 160 forwards the sequence of commands 115, 115' to instrument control module 136. Instrument control module 136 sends instructions to medical instruments 130 based on the sequence of commands 115, 115' from decision module 160. In this way, operators 110, 110' (who may be, for example, a surgeon and nurse) can perform an operation while controlling medical instruments 130 using voice commands 115, 115'.

Decision module 160 uses an algorithm to determine which commands 115, 115' to accept and reject. Decision module 160 can recognize contradictory or duplicative commands 115, 115' and defer to commands 115, 115' from a preferred set. For example, if first operator 110 is identified as a surgeon and second operator 110' is identified as a nurse, decision module 160 can reject commands 115' from second operator 110' where they duplicate or contradict commands 115 from first operator 110. The algorithm may also direct decision module 160 to set the timing of the execution of commands 115, 115' based on practical realities of the instruments 130, patients, and operators 110, 110'. For example, decision module 160 can recognize a command 115, 115' that would take an extended period of time to execute and elect to execute that command 115, 115' earlier than commands 115, 115' issued before it. Decision module 160 may also recognize that certain commands 115, 115' need to be executed before other commands 115, 115' issued previously by operators 110, 110' (either due to biological factors relating to the patient, or mechanical factors related to instruments 130), and may reverse the order of those commands 115, 115' on that basis. Decision module 160 can also determine that executing two or more commands 115, 115' in combination will result in a safety hazard to the patient, and reject one or more commands 115, 115' on that basis. Decision module 160 may also alter the timing or execution of its commands 115, 115' by direction from operators 110, 110'.

In some embodiments, display 192 displays which commands 115, 115' were executed from each operator 110, 110'. Display 192 is driven by display module 190 which receives information about which commands 115, 115' were executed from decision module 160. Operators 110, 110' can determine which of their commands 115, 115' were executed to control medical instruments 130 by viewing display 192. Operators 110, 110' can also determine which commands 115, 115' were executed by listening for verification sound 194 generated by speaker 196. Sound generating module 195 operates speaker 196 to issue verification sound 194 based on information it receives from decision module 160. For example, sound generating module 195 may emit one sound 194 every time a command 115 from first operator 110 is executed and a different sound 194 every time a command 115' from second operator 110' is executed. Also, sound generating module 195 may emit a distinctive sound 194 when only a portion of a command 115,115' was executed, to notify operators 110, 110' of this condition. This way operators 110, 110' can keep track of which commands 115, 115' have been executed, even though controller 105 is executing a combination of their commands 115, 115' and rejecting some of those commands 115, 115'. Display 192 can display a visible alert (or speaker 196 can issue an audible alert) if commands 115, 115' conflict, are duplicative, or would result in an unsafe condition if executed in combination. In response to these alerts, operators 110, 110' can issue additional commands 115, 115' or instructions to system 300 to remedy these conditions.

Although the invention has been described with reference to embodiments herein, those embodiments do not limit the scope of the invention. Modifications to those embodiments or different embodiments may fall within the scope of the invention.

What is claimed is:

1. A multi-user voice controlled medical system, comprising:
   a controller comprising a first speech recognition module, a second speech recognition module, and a decision module;
   at least one medical device operable by the controller;
   a first microphone in communication with the first speech recognition module;
   a second microphone in communication with the second speech recognition module;
   the first speech recognition module generates a first set of commands from voice signals it receives from a first user using said first microphone;
   the second speech recognition module generates a second set of commands from voice signals it receives from a second user using said second microphone;
   the decision module receives the first and second sets of commands, accepts a subset of the commands in the first and second sets, rejects the remainder of the commands, and assembles a third set of commands comprising the accepted commands; and
   the controller executes the third set of commands to operate said at least one medical device.

2. The system of claim 1, wherein the first speech recognition module adds commands to the first set of commands only if the voice signals it receives from said first microphone match a pre-approved user's voice.

3. The system of claim 1, wherein the decision module accepts or rejects at least one command based on which of the first and second sets of commands it is in.

4. The system of claim 1, wherein the decision module accepts or rejects at least one command based on whether the command conflicts with a command in a different set.

5. The system of claim 1, further comprising:
   a display module that generates a visible alert when the decision module determines that a command conflicts with a command in a different set.

6. The system of claim 1, further comprising:
   a sound generating module that generates an audible alert when the decision module determines that a command conflicts with a command in a different set.

7. The system of claim 1, wherein the decision module accepts or rejects at least one command based on instructions from a user.

8. The system of claim 1, wherein the decision module only accepts a command from the second set if a confirmation of that command is in the first set.

9. The system of claim 1, wherein the decision module accepts or rejects at least one command based on a risk of an unsafe condition resulting from that command being executed in combination with a command in a different set.

10. The system of claim 1, further comprising:
    a display module that generates a visible alert when the decision module determines that a risk of an unsafe condition would result from a command being executed in combination with a command in a different set.

11. The system of claim 1, further comprising:
    a sound generating module that generates an audible alert when the decision module determines that a risk of an unsafe condition would result from a command being executed in combination with a command in a different set.

12. The system of claim 1, wherein the first and second microphones are components of wireless voice control headsets.

13. The system of claim 1, wherein the first and second microphones are ambient microphones.

14. The system of claim 1, wherein the at least one medical device is an insufflator, a suction device, a light source, a video camera, a video control unit, a pressure gauge, a pump, an electrosurgical unit, a surgical table, a telephone, room lights, a personal digital assistant, a room camera, or an endoscope.

15. The system of claim 1, wherein the first and second users generate the voice signals simultaneously to control the medical system.

16. A method of operating at least one medical device using voice commands from multiple users, comprising:
    (a) receiving a plurality of first voice signals from a first user using a first microphone;
    (b) recognizing a first set of commands from the first voice signals using a first speech recognition module;
    (c) receiving a plurality of second voice signals from a second user using a second microphone;
    (d) recognizing a second set of commands from the second voice signals using a second speech recognition module;
    (e) accepting a subset of commands from the first and second sets of commands and rejecting the remainder of the commands from the first set and second sets of commands;
    (f) assembling a third set of commands using the commands accepted in step (e); and
    (g) executing the third set of commands to operate at least one medical device.

17. The method of claim 16, further comprising:
    (h) comparing the first voice signals to a pre-approved user's voice subsequent to step (a); and
    (i) performing step (b) only if the first voice signals match a pre-approved user's voice.

18. The method of claim 16, wherein a command is accepted or rejected in step (e) based on which of the first and second sets of commands it is in.

19. The method of claim 16, wherein a command is accepted or rejected in step (e) based on whether the command conflicts with a command in a different set of commands.

20. The method of claim 16, further comprising:
    (h) determining if a command in one set of commands conflicts with a command in a different set of commands subsequent to step (d); and
    (i) issuing an alert if a conflict is found in step (h).

21. The method of claim 20, further comprising:
    (j) rejecting one of the conflicting commands in step (e) upon being commanded to do so by a user.

22. The method of claim 20, wherein the alert is a visible alert.

23. The method of claim 20, wherein the alert is an audible alert.

24. The method of claim 16, wherein a command is accepted or rejected in step (e) based on a risk of an unsafe condition resulting from that command being executed in combination with a command in a different set.

25. The method of claim 16, further comprising:
    (h) determining if there is a risk of an unsafe condition resulting from a command being executed in combination with a command in a different set a command subsequent to step (d); and
    (i) issuing an alert if a risk is found in step (h).

26. The method of claim 25, further comprising:
(j) rejecting at least one of the commands in step (e) upon being commanded to do so by a user.

27. The method of claim 16, wherein the first and second microphones are components of wireless voice control headsets.

28. The method of claim 16, wherein the first and second microphones are ambient microphones.

29. The method of claim 16, wherein the at least one medical device is an insufflator, a suction device, a light source, a video camera, a video control unit, a pressure gauge, a pump, an electrosurgical unit, a surgical table, a telephone, room lights, a personal digital assistant, a room camera, or an endoscope.

\* \* \* \* \*